US007625736B2

(12) United States Patent
Schneerson et al.

(10) Patent No.: US 7,625,736 B2
(45) Date of Patent: *Dec. 1, 2009

(54) METHODS FOR PREPARING IMMUNOGENIC CONJUGATES

(75) Inventors: Rachel Schneerson, Bethesda, MD (US); Joanna Kubler-Kielb, Rockville, MD (US); Fathy Majadly, Frederick, MD (US); Stephen H. Leppla, Bethesda, MD (US); John B. Robbins, Bethesda, MD (US); Darrell T. Liu, Bethesda, MD (US); Joseph Shiloach, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 270 days.

This patent is subject to a terminal disclaimer.

(21) Appl. No.: 11/005,851

(22) Filed: Dec. 6, 2004

(65) Prior Publication Data

US 2005/0271675 A1 Dec. 8, 2005

Related U.S. Application Data

(63) Continuation-in-part of application No. PCT/US2004/017736, filed on Jun. 4, 2004.

(51) Int. Cl.
*A61K 39/385* (2006.01)
*A61K 39/07* (2006.01)
(52) U.S. Cl. .............................. 435/194.1; 435/197.11; 435/246.1; 530/405
(58) Field of Classification Search .................. None
See application file for complete search history.

(56) References Cited

U.S. PATENT DOCUMENTS

| 4,496,538 A | 1/1985 | Gordon |
| 5,521,290 A * | 5/1996 | Sivam et al. ............. 530/391.5 |
| 2006/0134143 A1 | 6/2006 | Schneerson et al. |

FOREIGN PATENT DOCUMENTS

| WO | WO 01/60412 A2 | 8/2001 |
| WO | WO 02/057422 * | 7/2002 |
| WO | WO 2005/000884 A1 | 1/2005 |

OTHER PUBLICATIONS

Schneerson R. et al. "Poly(.gamma.-D-glutamic acid) Protein Conjugates induce IgG antibodies in Mice to the Capsule of *Bacillus anthracis*: A Potential Addition to the Anthrax Vaccine", Jul. 2003, PNAS, vol. 100, pp. 8945-8950.*
Alkan, Sefik S., et al., "Antigen Recognition and the Immune Response: The Capacity of L-Tyrosine-Azobenzenearsonate to Serve as a Carrier for a Macromolecular Hapten," *The Journal of Immunology*, vol. 107, No. 2, pp. 353-358, Aug. 1971.
Goodman, Joel W., et al., "Immunochemical Studies on the Poly-γ-D-glutamyl Capsule of *Bacillus anthracis*. III. The Activity with Rabbit Antisera of Peptides Derived from the Homologous Polypeptide," *Biochemistry*, vol. 7, No. 2, pp. 706-710, Feb. 1968.
Klaus, G. G., et al., "The Immunological Properties of Haptens Coupled to Thymus-Independent Carrier Molecules. III. The role of the Immunogenicity and Mitogenicity of the Carrier in the Induction of Primary IgM Anti-Hapten Responses," *European Journal of Immunology*, vol. 5, No. 2, pp. 105-111, Feb. 1975 (Abstract).
Senyk, George, et al., "The Immune Response to Glucagon in Conjugated Form," *Immunochemistry*, vol. 9, pp. 97-110, 1972.
Emmanuel, J-P, et al., "Poly γ-D-Glutamic Acid as a Template for Functionalized Water-Soluble Biomaterials," *Abstracts of papers, American Chemical Society*, vol. 219, No. 1-2, 2000, p. BIOL 133.
Schneerson, Rachel, et al., "Poly(γ-D-Glutamic Acid) Protein Conjugates Induce IgG Antibodies in Mice to the Capsule of *Bacillus anthracis*: A Potential Addition to the Anthrax Vaccine," *PNAS*, vol. 100, No. 15, pp. 8945-8950, Jul. 22, 2003.
Leppla, Stephen H., et al., "Development of an Improved Vaccine for Anthrax," *The Journal of Clinical Investigation*, vol. 110, No. 2, pp. 141-144, Jul. 2002.
Welkos, Susan, et al., "The Role of Antibodies to *Bacillus anthracis* and Anthrax Toxin Components in Inhibiting the Early Stages of Infection by Anthrax Spores," *Microbiology*, vol. 147, pp. 1677-1685, Jun. 2001.
Rhie, Gi-Eun, et al., "A Dually Active Anthrax Vaccine that Confers Protection Against both *Bacilli* and Toxins," *PNAS*, vol. 100, No. 19, pp. 10925-10930, Sep. 16, 2003.
International Search Report, PCT Application No. PCT/US2004/017736, Dec. 8, 2004.
Kubler-Kielb et al., "Additional Conjugation Methods and immunogenicity of *Bacillus anthracis* Poly-γ-D-Glumatic Acid-Protein Conjugates," *Infection and Immunity* 74(8):4744-4749, 2006.
Devi et al., "*Cryptococcus neoformans* Serotype A Glucuronoxylomannan-Protein Conjugate Vaccines : Synthesis, Characterization, and Immunogenicity," *Infection and Immunity* 59(10):3700-3707, 1991.
King et al., "Preparation of Protein Conjugates via Intermolecular Hydrazone Linkage," *Biochemistry* 25(19):5774-5779, 1986.
Kozel et al., "mAbs to *Bacillus anthracis* capsular antigen for immunoprotection in anthrax and detection of antigenemia," *Proc. Natl. Acad. Sci. (USA)* 101(14):5

OTHER PUBLICATIONS

Pannifer et al., "Crystal structure of the anthrax lethal factor," *Nature* 414:229-233, 2001.

Pozsgay et al., "Protein conjugates of synthetic caccharides elicit higher levels of serum IgG lipopolysaccharide antibodies in mide than do those of the O-specific polysaccharide from *Shigella dysenteriae* type 1," *Proc. Natl. Acad. Sci. (USA)* 96:5194-5197, 1999.

Ramirez et al., Production, recovery and immunogenicity of the protective antigen from a recombinant strain of *Bacillus anthracis*, *J Ind Microbiol Biotechnol* 28:232-238, 2002.

Robbins et al., "Prevention of systemic infections, especially meningitis, caused by *Haemophilus influenzae* type b: Impact on public health and implications for other polysaccharide-based vaccines," *JAMA* 276:1181-1185, 1996.

Schneerson et al., "Preparation, Characterization, and Immunogenicity of *Haemophilus Influenzae* Type b Polysaccharide-Protein Conjugates," *The Journal of Experimental Medicine* 132:361-376, 1980.

Shinefield et al., "Use of a *Staphylococcus aureus* conjugate vaccine in patients receiving hemodialysis," *N Engl J Med* 346:491-496, 2002.

Apr. 3, 2007 Office action from U.S. Appl. No. 10/559,825.

Final Office action from U.S. Appl. No. 10/559,825, dated Nov. 28, 2007.

Office action dated Feb. 18, 2009 in U.S. Appl. No. 10/559,825.

* cited by examiner

METHODS FOR PREPARING IMMUNOGENIC CONJUGATES

CROSS REFERENCE TO RELATED APPLICATION

This application is a continuation-in-part of PCT International Application No. PCT/US04/017736, filed Jun. 4, 2004, which is incorporated herein by reference in its entirety.

BACKGROUND

Immunogenic conjugates have been made by forming a Schiff base between a linear alkylaldehyde and a linear alkylamine. However, the linkages in such conjugates are reversible at physiological pH (pH of about 6 to about 8) unless treated with sodiumborohydride to convert the compounds to diakylamines. In addition, antigen-carrier conjugation via alkyl-aldehyde and amine by reductive amination is commonly used. King et al., Preparation of Protein Conjugates via Intermolecular Hydrazone Linkage, *Biochemistry* 1986, 25, 5774-5779 describes a method for conjugating proteins that involves forming a hydrazone linkage between two proteins, but the hydrazone linkage is reversible and must be subject to reduction to form a more stable hydrazide bond. However, the reduction reaction used in all of these conjugation methods to improve stability typically involves a long exposure to boron-hydride. However, in the case of disulfide-containing carrier proteins and antigens, prolonged exposure to boron-hydride is a potential problem since it can also reduce the disulfide bonds in the carrier protein and alter its structure. Thus, it would be advantageous to have immunogenic conjugates that are not reversible at physiological pH, and that do not require reduction with boron-hydride.

SUMMARY

Disclosed herein is a method for making an immunogenic conjugate that includes a hapten or an antigen covalently linked to a carrier. The method includes reacting a first agent with a dihydrazide resulting in a hydrazino-modified first agent, wherein the first agent is a hapten, an antigen or a carrier; reacting a second agent with a benzaldehyde compound resulting in a benzaldehyde-modified second agent, wherein the second agent is a hapten, an antigen or a carrier, provided that the first agent or the second agent is a carrier; and reacting the hydrazine-modified first agent with the benzaldehyde-modified second agent resulting in an immunogenic conjugate comprising a hapten or an antigen covalently linked to a carrier via a hydrazone linkage.

Also disclosed herein is an immunogenic conjugate comprising a structure represented by formula I:

X-L-Z wherein X is a carrier;

Z is a hapten or an antigen; and

L is a linking group covalently bonded to X and Z, and comprising a hydrazone bond, a hydrazo bond, and a benzoylene moiety.

DETAILED DESCRIPTION OF SEVERAL EXAMPLES

I. Abbreviations

| | |
|---|---|
| ADH: | adipic acid dihydrazide |
| AT: | anthrax toxin |
| ATR: | anthrax toxin receptor |
| EDAC: | 1-ethyl-3-(3-dimethylaminopropyl)carbodiimide-HCl |
| EF: | edema factor |
| γPGA: | poly-γ-glutamic acid capsule from a *Bacillus* |
| γDPGA: | poly-γ-D-glutamic acid capsule from *B. anthracis* |
| γLPGA: | poly-γ-L-glutamic acid capsule from a *Bacillus* |
| GLC-MS: | gas-liquid chromatography-mass spectrometry |
| kDa: | kilodaltons |
| LC-MS: | liquid chromatography-mass spectrometry |
| LeTx: | lethal toxin |
| LF: | lethal factor |
| LPS: | lipopolysaccharide |
| MALDI-TOF: | matrix-assisted laser desorption ionization time-of-flight |
| μg: | microgram |
| μl: | microliter |
| PA: | protective antigen |
| PBS: | phosphate buffered saline |
| rEPA: | recombinant *Pseudomonas aeruginosa* exotoxin A |
| rPA: | recombinant *B. anthracis* protective antigen |
| SBAP: | succinimidyl 3-(bromoacetamido) propionate |
| SFB: | succinimidylformylbenzoate |
| SPDP: | N-hydroxysuccinimide ester of 3-(2-pyridyl dithio)-propionic acid |
| SLV: | succinimidyllevulinate |
| TT: | tetanus toxoid |

II. Terms

Unless otherwise noted, technical terms are used according to conventional usage. Definitions of common terms in molecular biology may be found in Benjamin Lewin, *Genes VII,* published by Oxford University Press, 2000 (ISBN 019879276X); Kendrew et al. (eds.), *The Encyclopedia of Molecular Biology,* published by Blackwell Publishers, 1994 (ISBN 0632021829); and Robert A. Meyers (ed.), *Molecular Biology and Biotechnology: a Comprehensive Desk Reference,* published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are the only vaccine adjuvants approved for human use. An aluminum hydrogel (available from Brentg Biosector, Copenhagen, Denmark is another common adjuvant).

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that may be specifically bound by the products of specific humoral or cellular immunity, such as an antibody molecule or T-cell receptor. Antigens can be any type of biologic molecule including, for example, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

*Bacillus*: A genus of bacteria whose collective features include degradation of most substrates derived from plant and animal sources, including cellulose, starch, pectin, proteins, agar, hydrocarbons, and others; antibiotic production; nitrification; denitrification; nitrogen fixation; facultative lithotrophy; autotrophy; acidophily; alkaliphily; psychrophily, thermophily and parasitism. Spore formation, universally found in the genus, is thought to be a strategy for survival in the soil environment, wherein the bacteria predominate. Aerial distribution of dormant spores likely explains the occurrence of *Bacillus* species in most habitats examined.

*Bacillus Anthracis:* The etiologic agent of anthrax, *Bacillus anthracis* is a large, gram-positive, nonmotile, spore-forming bacterial rod. The virulence of *B. anthracis* is dependent on AT, and the γDPGA capsule. The genes for the toxin, and the capsule, are carried by plasmids, designated pX01 and pX02, respectively (Mikesell et al., *Infect. Immun.* 39:371-76, 1983; Vodkin et al., *Cell* 34:693-97, 1983; Green et al., *Infect. Immun.* 49:291-97, 1985).

AT is composed of three entities: PA (the binding subunit of AT), and two enzymes known as LF and EF (Mikesell et al., *Infect. Immun.* 39:371-76, 1983; Vodkin et al., *Cell* 34:693-97, 1983). PA is an 83 kDa protein that is the main protective constituent of anthrax vaccines. PA binds to the anthrax toxin receptor (ATR) on cells and is then proteolytically cleaved by the enzyme furin with release of a 20 kDa fragment (Bradley et al., *Nature* 414:225-29, 2001; Klimpel et al., *PNAS* 89:10277-81, 1992). The 63 kDa PA remnant ($PA_{63}$) features a second binding domain and binds to either EF, an 89 kDa protein, to form edema toxin, or LF, a 90 kDa protein, to form lethal toxin (LeTx) (Leppla et al., *Salisbury Med. Bull. Suppl.* 68:4143, 1990). The resulting complex is internalized into the cell within endosomes (Singh et al., *Infect. Immun.* 67:1853-59, 1999; Friedlander, *J. Biol. Chem.* 261:7123-26, 1986).

The γDPGA capsule of *B. anthracis* serves as an essential virulence factor during anthrax infection, inhibiting host defense mechanisms through inhibition of phagocytosis of the vegetative cells by macrophages. While other *Bacillus* produce γPGA in a mixture of both D- and L-forms, only *B. anthracis* is known to synthesize it exclusively in a D-conformation (Kovacs et al., *J. Chem. Soc.* 4255-59, 1952). When injected, γDPGA has been shown to be a poor immunogen (Eisner, *Schweiz. Z. Pathol. Bakteriol.* 22:12944, 1959; Ostroff et al., *Proc. Soc. Exp. Biol. Med.* 99:34547, 1958). The capsule also shields the vegetative form of *B. anthracis* from agglutination by monoclonal antibodies to its cell wall polysaccharide (Ezzell et al., *J. Clin. Microbiol.* 28:223-31, 1990).

Carrier: An immunogenic molecule to which a hapten or an antigen such as a homopolymer of γPGA, can be bound. When bound to a carrier, the bound molecule may become more immunogenic. Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al, *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached.

Examples of bacterial products for use as carriers include bacterial toxins, such as *B. anthracis* PA (including fragments that contain at least one antigenic epitope and analogs or derivatives capable of eliciting an immune response), LF and LeTx, and other bacterial toxins and toxoids, such as tetanus toxin/toxoid, diphtheria toxin/toxoid, *P. aeruginosa* exotoxin/toxoid/, pertussis toxin/toxoid, and *C. perfringens* exotoxin/toxoid. Viral proteins, such as hepatitis B surface antigen and core antigen can also be used as carriers.

Covalent Bond: An interatomic bond between two atoms, characterized by the sharing of one or more pairs of electrons by the atoms. The terms "covalently bound" or "covalently linked" refer to making two separate molecules into one contiguous molecule. The terms include reference to joining a hapten or antigen indirectly to a carrier molecule, with an intervening linker molecule.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

γPGA: A homopolymer of glutamic acid residues linked by γ peptide bonds. The glutamic acid residues constituting the γPGA homopolymer can be solely in the L-form (γLPGA) or the D-form (γDPGA). When the form of the glutamic acid residues constituting the γPGA homopolymer can be either the L-form or the D-form, or when the two forms are mixed in a single molecule, the term γPGA is used. The weakly immunogenic and antiphagocytic capsule found on many species of *Bacillus,* which disguises the bacilli from immune surveillance, consists of γPGA.

γPGA Conjugate: A naturally occurring γPGA polypeptide produced by *B. anthracis* or another *Bacillus* species or strain covalently linked to a carrier, as well as conjugates of a carrier with a polypeptide fragment, synthetic polypeptide, or chemically modified derivative of a γPGA polypeptide. In some embodiments, the γPGA conjugate will comprise a conjugate of a carrier protein with a synthetic γPGA polypeptide having a selected peptide length and corresponding to a portion of a γPGA polypeptide from *B. anthracis* or another *Bacillus* species or strain that possesses a γPGA capsule.

Hapten: A molecule, typically a small molecule, which is not by itself an immunogen but that can combine specifically with an antibody, but is incapable of being immunogenic except in combination with a carrier molecule.

Homopolymer: This term refers to a polymer formed by the bonding together of multiple units of a single type of molecular species, such as a single monomer (for example, an amino acid).

Immune Response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically Effective Dose: An immunologically effective dose of the γPGA conjugates of the disclosure is therapeutically effective and will prevent, treat, lessen, or attenuate the severity, extent or duration of a disease or condition, for example, infection by *B. anthracis.*

Inhibiting or Treating a Disease: Inhibiting the full development of a disease or condition, for example, in a subject who is at risk for a disease such as anthrax. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Opsonin: A macromolecule that becomes attached to the surface of a microbe and can be recognized by surface receptors of neutrophils and macrophages and that increases the efficiency of phagocytosis of the microbe. Opsonins include IgG antibodies, which are recognized by the Fcγ receptor on phagocytes, and fragments of complement proteins, which are recognized by CR1 (CD35) and by the leukocyte integrin Mac-1.

Opsonophagocytosis: The process of attaching opsonins to microbial surfaces to target the microbes for phagocytosis.

PA-based Immunogen: A term used herein to refer to all forms of PA which are useful in immunogenic compositions and/or methods of the disclosure, including unmodified native or recombinant *B. anthracis* PA, or a variant or fragment thereof. Variants and fragments of PA are effective to elicit an anti-PA immune response in a subject to whom they are administered.

Pharmaceutically Acceptable Carriers: The pharmaceutically acceptable carriers (vehicles) useful in this disclosure are conventional. *Remington's Pharmaceutical Sciences,* by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents. The term "pharmaceutically acceptable carrier" should be distinguished from "carrier" as described above in connection with a hapten/carrier conjugate or an antigen/carrier conjugate.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protective Antigen (PA): One of the three components of the anthrax toxin. PA is a secreted nontoxic protein with a molecular weight of 83 kDa and is the major protective constituent of anthrax vaccines. PA binds to the ATR on cells and is then proteolytically cleaved by the enzyme furin with release of a 20 kDa fragment (Bradley et al., *Nature* 414:225-29, 2001; Klimpel et al., *PNAS* 89:10277-81, 1992). The 63 kDa PA remnant ($PA_{63}$) features a second binding domain and binds to either EF, an 89 kDa protein, to form edema toxin, or LF, a 90 kDa protein, to form lethal toxin (LeTx). The sequence of PA is known, for example, as encoded by bases 143779 to 146073 of GenBank Accession No. NC 007322 (plasmid pXO1; SEQ ID NOs: 2 and 3, nucleic and amino acid sequences, respectively).

Protein: A molecule, particularly a polypeptide, comprised of amino acids.

Purified: The term "purified" does not require absolute purity; rather, it is intended as a relative term. Thus, for example, a purified peptide, protein, γPGA conjugate, or other active compound is one that is isolated in whole or in part from proteins or other contaminants. Generally, substantially purified peptides, proteins, γPGA conjugates, or other active compounds for use within the disclosure comprise more than 80% of all macromolecular species present in a preparation prior to admixture or formulation of the peptide, protein, γPGA conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, γPGA conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Therapeutically Effective Amount: A quantity of a specified agent sufficient to achieve a desired effect in a subject being treated with that agent. For example, this may be the amount of a γDPGA conjugate useful in increasing resistance to, preventing, ameliorating, and/or treating infection and disease caused by *B. anthracis* infection in a subject. Ideally, a therapeutically effective amount of an agent is an amount sufficient to increase resistance to, prevent, ameliorate, and/or treat infection and disease caused by *B. anthracis* infection in a subject without causing a substantial cytotoxic effect in the subject. The effective amount of an agent useful for increasing resistance to, preventing, ameliorating, and/or treating infection and disease caused by *B. anthracis* infection in a subject will be dependent on the subject being treated, the severity of the affliction, and the manner of administration of the therapeutic composition.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

As detailed above, immunogenic conjugates disclosed herein may have a structure as represented by formula I. The conjugate may be a hapten/carrier conjugate or an antigen/carrier conjugate. The hapten, antigen, carrier, and linking group (L) shall be described in more detail below. Any specific combination of hapten/antigen, carrier and linking group (L) may be selected from the specific haptens, antigens, carriers and linking groups that are listed below.

An example of a conjugate structure is shown below in formulae II and III wherein the carrier is a protein (an antigen is shown in formulae II or III but a hapten could be substituted for the antigen):

Pr—NH—C(O)—($R^2$)$_y$—$C_6H_4$—CH=N—NH—C(O)—(C($R^6$)$_2$)$_z$—C(O)—NH—NH-Antigen Antigen-NH—C(O)—($R^2$)$_y$—$C_6H_4$—CH=N—NH—C(O)—(C($R^6$)$_2$)$_z$—C(O)—NH—NH—Pr wherein $R^2$ is —($CH_2$)$_n$—C(O)—, or —($CH_2$)$_n$—N(H)—C(O)—; y is 0 or 1; $C_6H_4$ is a benzene ring; n is 1 to 6; Pr is protein; z is 1 to 10; and each $R^6$ is independently hydrogen, or alkyl.

The conjugate structure includes a hydrazone bond (=N—NH—), a hydrazo bond (—NH—NH—), and a benzoylene moiety —C(O)—$C_6H_4$—.

A particular example of a conjugate is shown below in formula IV (adipic acid dihydrazide is the derivatizing group for the carrier protein and succinimidylformylbenzoate is the derivatizing group for the antigen):

Antigen—NH—C(O)—C$_6$H$_4$—CH=N—NH—C(O)—(CH$_2$)$_4$—C(O)—NH—NH—Pr

The hapten or antigen may be any hapten or antigen as generally described above. Illustrative examples of haptens or antigens include peptide, protein, polysaccharide, glycolipid, glycoprotein, or fragments thereof. The hapten may be a subunit, fragment or element of, or derived from, an antigen. For example, the hapten or antigen may be an antigenic polypeptide of a pathogenic organism, such as a viral or bacterial agent that produces undesirable symptoms in a subject following exposure. The hapten or antigen may for example be an attenuated virus, bacteria and/or parasite. Mixtures thereof are also contained within the present disclosure. The hapten or antigen may furthermore comprise only a part of a microorganism selected from the group consisting of viruses, bacteria and parasites. For example such a part may be a viral capsid. Alternatively, the hapten or antigen may only comprise one or more molecules, which have been derived from viruses, bacteria and parasites, such as for example polypeptides, peptides or nucleic acid sequences. Furthermore, the hapten or antigen may comprise molecules such as for example polypeptides, peptides or nucleic acid sequences, which comprise only fragments of viral, bacterial and parasite derived polypeptides, peptides or nucleic acid sequences. Such molecules may comprise more than one fragment.

The antigenic polypeptide can be that of a rotavirus, or of a virus other than a rotavirus. A non limiting, and far from exhaustive list of such other viruses includes Adeno-associated virus, Adenovirus, Avian infectious bronchitis virus, Baculovirus, Chicken pox, Corona virus, Cytomegaloviruis, Distemper, Enterovirus, Epstein Barr virus, Feline leukemia virus, Flavivirus, Foot and mouth disease virus, Hepatitis A, Hepatitis B, Hepatitis C, Hepatitis E, Herpes species, Herpes simplex, *Influenza* virus, HIV-1, HIV-2, HTLV 1, *Influenza* A and B, Kunjin virus, Lassa fever virus, LCMV (lymphocytic choriomeningitis virus), lentivirus, Measles, Mengo virus, Morbillivirus, Myxovirus, Papilloma virus, Parovirus, Parainfluenza virus, Paramyxovirus, Parvovirus, Poko virus, Polio virus, Polyoma tumour virus, pseudorabies, Rabies virus, Reovirus, Respiratory syncytial virus, retrovirus, rhinovirus, Rinderpest, Rotavirus, Semliki forest virus, Sendai virus, Simian Virus 40, Sindbis virus, SV5, Tick borne encephalitis virus, Togavirus (rubella, yellow fever, dengue fever), Vaccinia virus, Venezuelan equine encephalomyelitis, Vesicular stomatis virus, metapneumovirus, norovirus, SARS virus, smallpox virus, picornaviruses, varicella zoster, and West Nile virus.

Alternatively, the antigenic polypeptide can be that of a bacteria or other pathogenic organism. Exemplary bacterial polypeptides include those of *Achromobacter xylosoxidans*, *Acinetobacter calcoaceticus*, preferably *A. anitratus*, *A. haemolyticus*, *A. alcaligenes*, and *A. Iwoffii*, *Actinomyces israelii*, *Aeromonas hydrophilia*, *Alcaligenes* species, preferably *A. faecalis*, *A. odorans* and *A. denitrificans*, *Arizona hinshawii*, *Bacillus anthracis*, *Bacillus cereus*, *Bacteroides fragilis*, *Bacteroides melaninogenicus*, *Bordetella pertussis*, *Borrelia burgdorferi*, *Borrelia recurrentis*, *Brucella* species, preferably *B. abortus*, *B. suis*, *B. melitensis* and *B. canis*, *Calymmatobacterium granulomatis*, *Campylobacter coli* (e.g., the CjaA polypeptide), *Campylobacter fetus* ssp. *intestinalis*, *Campylobacter fetus* ssp. *jejuni*, *Chlamydia* species, preferably *C. psittaci* and *C. trachomatis*, *Chromobacterium violaceum*, *Citrobacter* species, preferably *C. freundii* and *C. diversus*, *Clostridium botulinum*, *Clostridium perfringens*, *Clostridium difficile*, *Clostridium tetani*, *Corynebacterium diphtheriae*, *Corynebacterium*, preferably *C. ulcerans*, *C. haemolyticum* and *C. pseudotuberculosis*, *Coxiella burnetii*, *Edwardsiella tarda*, *Eikenella corrodens*, *Enterobacter*, preferably *E. cloacae*, *E. aerogenes*, *E. hafniae* (also named *Hafnia alvei*) and *E. agglomerans*, *Erysipelothrix rhusiopathiae*, *Escherichia coli*, *Flavobacterium meningosepticum*, *Francisella tularensis*, *Fusobacterium nucleatum*, *Gardnerella vaginalis*, *Haemophilus ducreyi*, *Haemophilus influenzae*, *Helicobacter* species (e.g., the UreB polypeptide of *H. pylori*), *Klebsiella* species, preferably *K. pneumoniae*, *K. ozaenae* og *K. rhinoscleromatis*, *Legionella* species, *Leptospira interrogans*, *Listeria monocytogenes*, *Moraxella* species, preferably *M. lacunata* and *M. osloensis*, *Mycobacterium bovis*, *Mycobacterium leprae*, *Mycobacterium tuberculosis* (e.g., the CFP 10 polypeptide), *Mycoplasma* species, preferably *M. pneumoniae*, *Neisseria gonorrhoeae*, *Neisseria meningitidis*, *Nocardia* species, preferably *N. asteroides* and *N. brasiliensis*, *Pasteurella haemolytica*, *Pasteurella multocida*, *Peptococcus magnus*, *Plesiomonas shigelloides*, *Pneumococci*, *Proteus* species, preferably *P. mirabilis*, *P. vulgaris*, *P. rettgeri* and *P. morganii* (also named *Providencia rettgeri* and *Morganella morganii* respectively), *Providencia* species, preferably *P. alcalifaciens*, *P. stuartii* and *P. rettgeri* (also named *Proteus rettgeri*), *Pseudomonas aeruginosa*, *Pseudomonas mallei*, *Pseudomonas pseudomallei*, *Rickettsia*, *Rochalimaia henselae*, *Salmonella* species, preferably *S. enteridis*, *S. typhi* and *S. derby*, and most preferably *Salmonella* species of the type *Salmonella* DT104, *Serratia* species, preferably *S. marcescens*, *Shigella dysenteriae*, *S. flexneri*, *S. boydii* and *S. sonnei*, *Spirillum minor*, *Staphylococcus aureus*, *Staphylococcus epidermidis*, *Staphylococcus saprophyticus*, *Streptobacillus moniliformis*, *Streptococcus*, preferably *S. faecalis*, *S. faecium* and *S. durans*, *Streptococcus agalactiae*, *Streptococcus pneumoniae*, *Streptococcus pyogenes* (e.g., the Sfb1 polypeptide), *Treponema carateum*, *Treponema pallidum*, *Treponema pertenue*, preferably *T. pallidum*, *Ureaplasma urealyticum*, *Vibrio cholerae*, *Vibrio parahaemolyticus*, *Yersinia enterocolitica*, and *Yersinia pestis*.

Parasitic haptens or antigens may for example be selected from Malaria (*Plasmodium. falciparum*, *P. vivax*, *P. malariae*), Schistosomes, Trypanosomes, Leishmania, Filarial nematodes, Trichomoniasis, Sarcosporidiasis, Taenia (*T. saginata*, *T. solium*), Leishmania, Toxoplasma gondii, Trichinelosis (*Trichinella spiralis*) or Coccidiosis (*Eimeria* species).

Illustrative fungal haptens or antigens could be derived a fungus selected from *Cryptococcus neoformans*, *Candida albicans*, *Aspergillus fumigatus* and *Coccidioidomycosis*.

The hapten or antigen may also be derived from any animal, including for example vertebrates. For example the hapten or antigen may comprise components derived from ovalbumin, keyhole limpet hemocyanin and sperm-whale myoglobulin.

In a specific example, *Bacillus* capsular γPGA polypeptide—carrier conjugates (γPGA conjugates) prepared by the presently described methods disclosed herein. The γPGA conjugates elicit an immune response in a subject, and inhibit or treat infection and/or disease caused by *B. anthracis* or other bacilli.

The weakly immunogenic and antiphagocytic γPGA capsule, which consists of glutamic acid residues linked by γ peptide bonds, disguises the *bacilli* from immune surveillance. As disclosed herein, *Bacillus* capsular γPGA polypeptides include, but are not limited to, *B. anthracis*, *B. licheni-* formis, B. pumilus, and B. subtilis γPGA polypeptides. All Bacillus besides B. anthracis that are known to produce γPGA make a mixture of both the D- and L-forms, whereas B. anthracis produces exclusively γDPGA. In one embodiment, the γPGA conjugates disclosed herein are γLPGA conjugates. In another embodiment, the γPGA conjugates are γDPGA conjugates. In a specific, non-limiting example, the γDPGA conjugate is a B. anthracis γDPGA conjugate.

Bacillus capsular γPGA polypeptides can be isolated by many methods well known in the art, such as salt fractionation, phenol extraction, precipitation with organic solvents (for example, hexadecyltrimethylammonium bromide (cetavlon) or ethanol), affinity chromatography, ion-exchange chromatography, hydrophobic chromatography, high performance liquid chromatography, gel filtration, isoelectric focusing, and the like. In one specific, non-limiting example, Bacillus capsular γPGA polypeptides are extracted from the culture supernatant of growing bacilli by cetavlon precipitation, acidification to pH 1.5, precipitation with ethanol, and passage through a 2.5×100 cm Sepharose CL4B column in 0.2M NaCl. The compositions of extracted γPGA polypeptides are determined by methods well known in the art, such as $^1$H-nuclear magnetic resonance (NMR) spectroscopy and $^{13}$C-NMR spectroscopy; while their enantiomeric confirmations can be determined by gas-liquid chromatography-mass spectrometry (GLC-MS).

Synthetic γPGA polypeptides of varying lengths (for example, about 5, 10, 15, or 20 residues) having either the D- or L-configuration can be readily synthesized by automated solid phase procedures well known in the art. Suitable syntheses can be performed by utilizing "T-boc" or "F-moc" procedures. Techniques and procedures for solid phase synthesis are described in *Solid Phase Peptide Synthesis: A Practical Approach*, by E. Atherton and R. C. Sheppard, published by IRL, Oxford University Press, 1989. In specific, non-limiting examples, the synthetic γPGA polypeptide includes about 1 to about 20 glutamic acid residues, such as about 10 to about 15 glutamic acid residues, or about 10 glutamic acid residues. The compositions and purity of synthetic γPGA polypeptides can be determined by GLC-MS and matrix-assisted laser desorption ionization time-of-flight (MALDI-TOF) spectrometry.

In a further example, the hapten or antigen may also comprise more than one different polypeptide and/or peptide, such as 2, for example 3, such as 4, for example 5, such as 6, for example 7, such as 8, for example 9, such as 10, for example more than 10 different polypeptides. In a further example, the hapten or antigen comprises or essentially consists of an organism, preferably a microorganism or part of an organism, preferably a microorganism and accordingly the hapten or antigen may comprise a very large number of different polypeptides, such as more than 100, for example more than 500, such as more than 1000, for example more than 2500. It is also contained within the present disclosure that the hapten or antigen may essentially consist of or consist of one or more polypeptides and/or peptides.

Examples of suitable antigens or haptens include any antigen or hapten that is used as a vaccine for a single disease ("single antigen") or two or more diseases simultaneously ("mixed antigen"). The mixed antigen may be a mixture of two or more antigens or haptens, or an antigen that has antigenicities for two or more diseases simultaneously, e.g., a recombinant protein. As an antigen, there may be used an entire organism, e.g., a viral or bacterial whole cell, or a part of the organism, e.g., a certain protein having an antigenicity.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, semi-synthetic or synthetic materials containing one or more functional groups, for example primary and/or secondary amino groups, azido groups, hydroxyl groups, or carboxyl groups, to which a reactant moiety can be attached. The carrier can be water soluble or insoluble, and in some embodiments is a protein or polypeptide. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it induces is not of benefit by itself.

Specific, non-limiting examples of water soluble polypeptide carriers include, but are not limited to, natural, semi-synthetic or synthetic polypeptides or proteins from bacteria or viruses. In one embodiment, bacterial products for use as carriers include bacterial wall proteins and other products (for example, streptococcal or staphylococcal cell walls), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: B. anthracis PA (for example, as encoded by bases 143779 to 146073 of GenBank Accession No. NC 007322, herein incorporated by reference), including variants that share at least 90%, at least 95%, or at least 98% amino acid sequence homology to PA, fragments that contain at least one antigenic epitope, and analogs or derivatives capable of eliciting an immune response; B. anthracis LF (for example, as encoded by the complement of bases 149357 to 151786 of GenBank Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *P. aeruginosa* exotoxin/toxoid/(for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094). Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins.

Specific, non-limiting examples of water insoluble carriers include, but are not limited to, aminoalkyl agarose (for example, aminopropyl or aminohexyl SEPHAROSE; Pharmacia Inc., Piscataway, N.J.), aminopropyl glass, cross-linked dextran, and the like, to which a reactive moiety can be attached. Other carriers can be used, provided that a functional group is available for covalently attaching a reactive group.

The linking group (L) is derived from the covalent linkage formed from the dihydrazide derivatization and the benzaldehyde derivatization. According to certain examples, the linking group may have a structure represented by formula V:

$$-C(O)-(R^2)_y-C_6H_4-CH=N-NH-C(O)-(C(R^6)_2)_z-C(O)-NH-NH-$$

wherein $R^2$, $R^6$, z and y are the same as in formulae II and III above.

The linking group may include a spacer moiety positioned between the hydrazone bond and the hydrazo bond. The spacer moiety typically has a linear backbone chain structure. The linear backbone chain may include, for example, 3-10 carbon atoms. In particular, the linear backbone chain may be 6 carbon atoms in length. In certain examples, the spacer moiety has a structure represented by the formula VI:

—C(O)—(C(R$^6$)$_2$)$_z$—C(O)— wherein R$^6$ and z are the same as in formula II and III above.

The linking group also includes a benzoylene moiety (—C$_6$H$_4$—C(O)—). The benzoylene moiety is derived from the benzaldehyde linker compound as described below in more detail.

Although not bound by any theory, it is believed that the dihydrazide reactant provides a spacer moiety that may confer improved immunogenicity to the resulting conjugate. Although not bound by any theory, it is also believed that the formation of the Schiff-base moiety from the benzaldehyde compound linkage may improve the stability of the resulting conjugate by substantially diminishing the reversibility of the hydrazone linkage. In particular, the extensive resonance system of the aromatic ring and the carbonyl (—C(O)—) bonded to the benzene ring contributes to the stabilization of the conjugate. For example, immunogenic conjugates produced by the methods disclosed are stable at a pH of about 6 to about 7.5 at room temperature or below, in the presence of glycerol (0.1-10%). The hydrazone linkage of the immunogenic conjugate can be reversed by high concentrations (above 1 M) of acetylhydrazide, and the hydrazone bond will be cleaved when heated in 6N HCl or 2N NaOH at 100° C. for 1 hour. Moreover, the immunogenic conjugates disclosed herein may provide superior immunogenicity compared to immunogenic conjugates prepared by prior art methods.

Also disclosed herein are methods for conjugating a hapten or antigen to a carrier molecule that involve initially derivatizing or "activating" the hapten or antigen and the carrier, and then reacting the resulting modified hapten or antigen and modified carrier together to form the conjugate. One of the derivatizations involves reacting a dihydrazide with the hapten, antigen or carrier. The other derivatization involves reacting a benzaldehyde compound with the hapten, antigen or carrier. In one example, the hapten or antigen is reacted with a dihydrazide and the carrier is reacted with a benzaldehyde compound. In an alternative example, the hapten or antigen is reacted with a benzaldehyde compound and the carrier is reacted with a dihydrazide. The modified hapten or antigen and the modified carrier are reacted together to form a conjugate having a structure as shown in formula I above.

A feature of the methods disclosed herein is that the hydrazone linkage in the conjugate of formula I does not require reduction to form a hydrazide bond. Moreover, the synthesis method is specific, does not cause any noticeable side-reaction, and a high yield is achievable.

The benzaldehyde may be reacted with the hapten, antigen or carrier (e.g., protein) under conditions sufficient to form a benzaldehyde-modified compound having a structure represented by the formula VII:

Hapten-NH—C(O)—(R$^2$)$_y$—C$_6$H$_4$—C(O)H or

Pr—NH—C(O)—(R$^2$)$_y$—C$_6$H$_4$—C(O)H wherein R$^2$ is —(CH$_2$)$_n$—C(O)—, or —(CH$_2$)$_n$—N(H)—C(O)—; y is 0 or 1; C$_6$H$_4$ is a benzene ring; n is 1 to 6; and Pr is protein. According to certain example, the benzaldehyde-modified protein can have a structure represented by the formula VIII:

Pr-Lys-NH—C(O)—(R$^2$)$_y$—C$_6$H$_4$—C(O)H wherein Lys is a lysine residue.

As is apparent from formulae VII and VIII, derivatization with the benzaldehyde compound typically occurs at least one free amino group of the hapten, antigen or carrier. Benzaldehyde-modified compounds that have been derivatized with succinimidyl-alkyl-benzaldehyde (SBA) are also referred to herein as "SBA-Pr", "SBA-antigen" and "SBA-carrier".

In general, benzaldehyde derivatization of the hapten, antigen or carrier can be accomplished by reacting the hapten, antigen or carrier at a concentration of about 5 to about 20 mg/mL, more particularly about 8 to about 14 mg/mL with the benzaldehyde compound dissolved in about 0.1 mL dimethylsulfoxide (DMSO). The reaction may be performed in a buffer at pH of about 7 to 8 in the presence of an appropriate amount of a phosphate, carbonate, glycerol and/or salt (e.g., NaCl). The volume of the DMSO can be less than about 10% of the reaction mixture. Adding 10% glycerol in the reaction mixture protects the protein from denaturation. The reaction proceeds at about 4 to about 25° C. (usually approximately 20° C.) for about 1 to about 5 hours while maintaining the pH with the addition of NaOH.

In one example in which the hapten, antigen or carrier is a protein, the amount of benzaldehyde compound that may be used can be calculated from the amount of protein and its lysine residue content and, for instance, should not exceed the total amount of lysine residue content. For example, the molecular mass of bovine serum albumin (BSA) is 64 kDa and it contains 60 lysine/BSA. Ten mg of BSA corresponds to 0.156 micromoles containing 9.3 micromole of lysine residue. Thus, the amount of succinimidyl-alkyl-benzaldehyde (SBA) (Mw, 247) that could be used should not exceed 9 micromoles (2.2 mg). At a pH of 7.4, that amount of SBA derivatizes the lysine amino group of the BSA without any substantial side reactions.

Illustrative benzaldehyde compounds that may be suitable for use in the methods disclosed herein can be represented by the formula IX:

R$^3$—C(O)—(R$^2$)$_y$—C$_6$H$_4$—C(O)H wherein R$^2$ is —(CH$_2$)$_n$—C(O)—, or —(CH$_2$)$_n$—N(H)—C(O)—; R$^3$ is hydrogen, succinimidyl-O—, succinimidyl, succinimidyl-N(H)—O—, alkyl, or amino; y is 0 or 1; C$_6$H$_4$ is a benzene ring; and n is 1 to 6. According to certain examples, the benzaldehyde compound may be succinimidylformylbenzoate (SFB), succinimidyl-O—C(O)—(CH$_2$)$_n$—C(O)—C$_6$H$_4$—CHO, or succinimidyl-O—C(O)—(CH$_2$)$_n$—N(H)—C(O)—C$_6$H$_4$—CHO.

The dihydrazide may be reacted with the hapten, antigen or carrier (e.g., protein) under conditions sufficient to form a dihyrazide-modified compound having a structure represented by the formula X:

Antigen-CO—NH—NH—C(O)—(C(R$^6$)$_2$)$_z$—C(O)—NH—NH$_2$ or

Pr—CO—NH—NH—C(O)—(C(R$^6$)$_2$)$_z$—C(O)—NH—NH$_2$ wherein R$^6$ and z are the same as in formulae II and III.

Dihydrazide-modified compounds that have derivatized with ADH are also referred to herein as "AH-antigen", "AH-protein" or "AH-carrier".

Methods for derivatizing antigens, haptens and carriers with a dihydrazide are known in the art (see, e.g., Schneerson et al., *J. Exp. Med.* 152:361-76, 1980; Kubler-Kielb et al., *J. Bacteriol.* 186(20):6981-901, October 2004; Shrivastav, *J. Immunoassay Immunochem.* 25(3):215-25, 2002). In certain examples, the derivatization with the dihydrazide is a single-step process in the sense that one of the hydrazino ($-NHNH_2$) moieties of the dihydrazide directly forms an amide bond with a free carboxyl group of the hapten, antigen or carrier. In other words, the hapten, antigen or carrier does not require an initial derivatization or modification with another agent prior to the reaction with the dihydrazide. One dihydrazide derivatization method involves reacting the hapten or antigen with the dihydrazide in the presence of a peptide coupling agent, preferably a water-soluble carbodiimide such as 1-ethyl-3-(3-dimethylaminopropyl)carbodiimide, 1-ethyl-3-(3-dimethylaminopropyl)-carbodiimide methiodide.

Illustrative dihydrazide compounds that may be suitable for use in the methods disclosed herein can be represented by the formula XI:

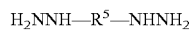

wherein $R^5$ is $-C(O)-(C(R^6)_2)_z-C(O)-$ (wherein z is 1 to 10; each $R^6$ is independently hydrogen, or alkyl). According to certain example, the dihydrazide may be a dicarboxylic acid dihydrazide such as adipic acid dihydrazide (ADH), succinic acid dihydrazide, suberic acid dihydrazide, sebacic acid dihydrazide, malonic acid dihydrazide, or glutaric acid dihydrazide.

The benzaldehyde-modified compound can be conjugated with the dihydrazide-modified by subjecting a reaction mixture of the benzaldehyde-modified compound and the dihydrazide-modified compound to conditions sufficient for formation of the hydrazone linkage. For instance, the benzaldehyde-modified compound can be mixed with the dihydrazide-modified compound and the pH kept at about 6.0 to about 7.0 with the addition of either NaOH or HCl for about 60 minutes. The reaction mixture may be transferred to a vial and tumbled for 24-48 hours at room temperature and passed through an appropriate sizing column (Sephadex) in a buffer containing 0.2 M NaCl, 0.05 M phosphate, 0.1% glycerol, and 1 mM EDTA. Other buffers can be used but they should contain the glycerol and EDTA. Fractions may be collected for analyses of protein and saccharide/peptide, antigenicity of both components and molecular size. Alternatively, dialysis/ultrafiltration can be used to separate the reagents from the conjugates.

In certain examples, the amount of AH-antigen to be used to conjugate with SBA-protein may be calculated from the AH content. For instance, AH-antigen with 5% AH contains 2.8 micromoles of AH/mg. To conjugate with 10 mg of BSA derivatized with SBA, about 2 to 3 mg of AH-antigen containing 5.6 to 8.4 micromoles of AH should be used. AH-antigen is dissolved in 0.1 mL of an appropriate solvent (DMSO, water or phosphate buffer, pH 7.0).

Following conjugation of the hapten to antigen to a carrier, the hapten-carrier conjugate or antigen-carrier conjugate can be purified by a variety of techniques well known to one of skill in the art. One goal of the purification step is to remove the unbound hapten or antigen from the conjugate. One method for purification, involving ultrafiltration in the presence of ammonium sulfate, is described in U.S. Pat. No. 6,146,902. Alternatively, the conjugates can be purified away from unreacted hapten/antigen and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry.

The conjugates disclosed herein may be included in pharmaceutical compositions (including therapeutic and prophylactic formulations), typically combined together with one or more pharmaceutically acceptable vehicles and, optionally, other therapeutic ingredients (for example, antibiotics, or anti-inflammatories).

Such pharmaceutical compositions can be administered to subjects by a variety of mucosal administration modes, including by oral, rectal, intranasal, intrapulmonary, or transdermal delivery, or by topical delivery to other surfaces. Optionally, the conjugate can be administered by non-mucosal routes, including by intramuscular, subcutaneous, intravenous, intra-atrial, intra-articular, intraperitoneal, or parenteral routes. In other alternative embodiments, the conjugate can be administered ex vivo by direct exposure to cells, tissues or organs originating from a subject.

To formulate the pharmaceutical compositions, the conjugate can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton Ind.) and IL-12 (Genetics Institute, Cambridge Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The conjugate can be dispersed in a base or vehicle, which can include a hydrophilic compound having a capacity to disperse the conjugate, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, crosslinking and the like. The vehicle can be provided in a variety of forms, including, fluid or viscous solutions, gels, pastes, powders, microspheres and films for direct application to a mucosal surface.

The conjugate can be combined with the base or vehicle according to a variety of methods, and release of the conjugate can be by diffusion, disintegration of the vehicle, or associated formation of water channels. In some circumstances, the conjugate is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the conjugate can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the conjugate can be brought about by including in the composition an agent which delays absorption, for example, monostearate salts and gelatin.

In certain embodiments, the conjugate can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the conjugate and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems,* J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the conjugate and/or other biologically active agent into a sterile vehicle that contains a basic dispersion medium and the required other ingredients from those enumerated herein. In the case of sterile powders, methods of preparation include vacuum drying and freeze-drying which yields a powder of the conjugate plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the conjugate can be delivered to a subject in a manner consistent with conventional methodologies associated with management of the disorder for which treatment or prevention is sought. In accordance with the disclosure herein, a prophylactically or therapeutically effective amount of the conjugate and/or other biologically active agent is administered to a subject in need of such treatment for a time and under conditions sufficient to prevent, inhibit, and/or ameliorate a selected disease (for example, anthrax) or condition or one or more symptom(s) thereof.

The subject matter of the present disclosure is further illustrated by the following non-limiting Examples.

EXAMPLES

Example 1

Materials and Methods

Bacterial Strains

*B. pumilus*, strain Sh18 (Goodman et al., *Biochem.* 7:706-10, 1968), and *B. anthracis* strain A34, a $pX01^-$, $pX02^+$ variant derived from the Ames strain by repeated passage at 43° C., are described by Klein et al. (*Science* 138:1331-33, 1962).

Poly-γ-glutamic Acid

γPGA was extracted from culture supernatants of *B. anthracis* or *B. pumilus* by acidification to pH 1.5, precipitation with ethanol, and passage through a 2×100 cm Sepharose CL-4B column in 0.2 M NaCl (Myerowitz et al., *Infect. Immun.* 8:896-900, 1973). The composition of each γPGA was confirmed by $^1$H-NMR and $^{13}$C-NMR and their enantiomeric compositions were determined by GLC-MS spectroscopy.

Analyses

Amino acid analyses were conducted by GLC-MS after hydrolysis with 6 N HCl, 150° C., 1 hour, derivatization to heptafluorobutyryl R-(−)isobutyl esters and assayed with a Hewlett-Packard apparatus (Model HP 6890) with a HP-5 0.32×30 mm glass capillary column, temperature programming at 8° C./min, from 125° C. to 250° C. in the electron ionization (106 eV) mode (MacKenzie, *J. Assoc. Off. Anal. Chem.* 70:151-60, 1987). Under these conditions, D-glutamic acid is separated from the L-enantiomer so that the ratio of each can be calculated based on the ratio of D-glutamic acid relative to L-glutamic acid residues in the protein (FIG. 1). The number of peptide chains in L-peptide conjugates was calculated by the relative increase of total L-glutamic acid relative to aspartic acid. Protein concentration was measured by the method of Lowry et al. (*J. Biol. Chem.* 193:266-73, 1951), free ε amino groups by Fields' assay (*Biochem. J.* 124:581-90, 1971), thiolation by release of 2-pyridylthio groups ($A_{343}$) (Carlsson et al., *Biochem. J.* 173:723-37, 1978), and hydrazide as reported by Schneerson et al. (*J. Exp. Med.* 152:361-76, 1980). SDS-PAGE employed 14% gels according to the manufacturer's instructions. Double immunodiffusion was performed in 1.0% agarose gel in PBS.

MALDI-TOF

Mass spectra were obtained with a PerSeptive BioSystems Voyager Elite DE-STR MALDI-TOF instrument (PE Biosystems, Framingham, Mass.) operated in the linear mode, 25 kV accelerating voltage and a 300 nanosecond ion extraction delay time. Samples for analysis were prepared by a "sandwich" of matrix and analyte. First, 1 μl matrix (saturated solution of sinnapinic acid made in 1:1 $CH_3CN$ and 0.1% trifluroacetic acid) was dried on the sample stage. Second, 1 μl of sample and an additional 1 μl of matrix was applied. After the "sandwich" was dried, the sample was placed in the mass spectrometer.

Antigens

BSA (Sigma Chemical Co., St. Louis, Mo.) was dialyzed against pyrogen-free water, sterile-filtered, and freeze-dried. Recombinant Protective Antigen from *B. anthracis* and recombinant exotoxin A from *P. aeruginosa* were prepared and characterized as described by Ramirez et al. (*J. Ind. Microbiol. Biotechnol.* 28:232-38, 2002) and Johansson et al. (*J. Biotechnol.* 48:9-14, 1996). Exemplary synthetic polypeptides of γPGA (AnaSpec, San Jose, Calif.) were synthesized by the method of Merrifield, with lengths of 5, 10, 15, or 20 residues. Their purity and authenticity were verified by GLC-MS, LC-MS and MALDI-TOF. γPGA polypeptides were bound to carrier proteins at either the C- or the N-termini (-C indicates that the C-terminus is free; N- indicates that the amino-terminus is free). All reactions were conducted in a pH stat under argon.

Type I: NBrAc-Gly$_3$-γDPGA$_n$-COOH(Br-Gly$_3$-γDPGA$_n$-C) NBrAc-Gly$_3$-γLPGA$_n$-COOH(Br-Gly$_3$-γLPGA$_n$-C)

Type II: NAc-L-Cys-Gly$_3$-γDPGA$_n$-COOH(Cys-Gly$_3$-γDPGA$_n$-C)  NAc-L-Cys-Gly$_3$-γLPGA$_n$-COOH(Cys-Gly$_3$-γLPGA$_n$-C)

Type III: NAc-γDPGA$_n$-Gly$_3$-L-Cys-CONH$_2$(N-γDPGA$_n$-Gly$_3$-Cys)  NAc-γLPGA$_n$-Gly$_3$-L-Cys-CONH$_2$(N-γLPGA$_n$-Gly$_3$-Cys)

Type IV: CHO-Gly3-γDPGA$_n$-COOH

Type V: NAc-γDPGA$_n$-Gly3-CO-AH  NAc-γDPGA$_n$-CO-AH

Type VI: NAc-γDPGA$_n$-Cys-CONH$_2$

Conjugation of BSA, rEPA and rPA with *B. anthracis* γDPGA and *B. pumilus* γDLPGA BSA, rEPA and rPA were derivatized with adipic acid dihydrazide with modifications (Schneerson et al., *J. Exp. Med.* 152:361-76, 1980). The pH was maintained at 7.0 and 0.1 M EDAC used. The products, BSA-AH, rEPA-AH and rPA-AH, contained 2.0-4.8% hydrazide.

γPGA was bound to rPA-AH or rEPA-AH with 0.01 M EDAC, the reaction mixture passed through a 1×90 cm Sephacryl S-1000 column in 0.2 M NaCl, and fractions reacting with anti-PA and anti-γDPGA by an identity line were pooled.

Conjugation of Type I Peptide with rPA Via Thioether Bond

Step 1: Derivatization of BSA, rEPA and rPA with SPDP

To rPA (30 mg) in 1.5 ml of Buffer A' (PBS, 3% glycerol, 0.005 M EDTA, pH 7.6), SPDP (10 mg) in 50 μl dimethyl sulfoxide (DMSO) was added in 10 μl aliquots and reacted for 1 hour at pH 7.6. The product, 2-pyridyldithio-propionyl-rPA (PDP-rPA) was passed through a 1×48 cm Sephadex G-50 column in Buffer A (PBS, 0.05% glycerol, 0.005 M EDTA, pH 7.6), and protein-containing fractions were pooled and assayed for thiolation, antigenicity, and molecular mass (Carlsson et al., *Biochem. J.* 173:723-37, 1978).

Step 2: Conjugation of PDP-protein with Type I Peptide

PDP-protein (24 mg) in 2 ml Buffer A was treated with 50 mM dithiothreitol for 30 minutes at room temperature and passed through a 1×48 cm Sephadex G-50 column in Buffer A. Fractions containing the 3-thiopropionyl-ε-Lys-NH$_2$-rPA (rPA-SH) were collected, concentrated to 1.5 ml and glycerol added to a final concentration of 3%. Br-Gly$_3$-γ-DPGA$_n$-C, 10 mg in 1 ml of Buffer A, was adjusted to pH 7.6 and rPA-SH added, incubated for 1 hour at room temperature (Inman et al., *Bioconj. Chem.* 2:458-63, 1991), transferred to a vial, capped and tumbled overnight at room temperature. Bromoacetamide, 0.5 mg in 50 μl Buffer A, was added to block unreacted thiols. After 30 minutes, the reaction mixture was passed through a 1×90 cm Sephacryl S-200 column in Buffer B (0.01 M phosphate, 0.2 M NaCl, 0.05% glycerol, pH 7.2). Fractions containing protein-γPGA were pooled and assayed for peptide and protein concentration, antigenicity, and molecular mass.

Products:

BSA contained 60, rPA contained 58 and rEPA contained 15 moles Lys per mole of protein, respectively. Under these conditions, 28 of 60 c-Lys-NH$_2$ of BSA, 50-55 of 58 of rPA and 15 of 15 of rEPA were derivatized with SPDP with retention of their antigenicity. Conjugation of BSA-SH, rPA-SH and rEPA-SH with Type I peptides yielded:
BSA-SH/Gly$_3$-γDPGA$_n$-C
BSA-SH/Gly$_3$-γLPGA$_n$-C
rEPA-SH/Gly$_3$-γDPGA$_n$-C
rPA-SH/Gly$_3$-γDPGA$_n$-C Conjugation With Type II, III and VI Peptides Step 1: Derivatization of Protein With SBAP rPA or rEPA (30 mg) in 1.5 ml of Buffer A' was adjusted to pH 7.2. SBAP (11 mg) in 50 μl DMSO was added in 10 μl aliquots (Inman et al., *Bioconj. Chem.* 2:458-63, 1991). After 60 minutes, the reaction mixture was passed through a 1×90 cm Sepharose CL-6B column in Buffer B. Fractions containing bromoacetamidopropionyl-ϵ-Lys-NH-rPA (Br-rPA) were collected and assayed for protein, free —$NH_2$, antigenicity, and molecular mass.

Step 2: Conjugation of Br-protein With Type II, III and VI Peptides

Type II, III or VI peptides, 5 to 15 mg in Buffer A, were adjusted to pH 7.6 with 1 N NaOH. Br-protein (25 mg) in 1.5 ml Buffer A' was added. After 1 hour, the reaction mixture was transferred to a vial, capped, and tumbled overnight at room temperature. β-mercaptoethanol (1 μl) was added to quench the remaining bromoacetyl groups in Br-protein. After 30 minutes, the reaction mixture was passed through 1×90 cm Sepharose CL-6B column in Buffer B. Fractions containing protein-γPGA were pooled and assayed for peptide and protein concentration, antigenicity, and molecular mass.

Products:

Under these conditions, 50-55 of 58 and 15 of 15 residues of ϵ-Lys-$NH_2$ of rPA and rEPA, respectively, were modified with SBAP. $rPA_{form}$ had 30 out of 58 ϵ-Lys-$NH_2$ free, and derivatization with SBAP converted essentially all 30 ϵ-Lys-$NH_2$ into the bromoacylated derivative, Br-$rPA_{form}$.

Conjugation of Br-rPA and Br-rEPA with Type II peptides yielded 4 conjugates:

rPA/S-Cys-$Gly_3$-γ$DPGA_n$-C
rPA/S-Cys-$Gly_3$-γ$LPGA_n$-C
rEPA/S-Cys-$Gly_3$-γ$DPGA_n$-C
rEPA/S-Cys-$Gly_3$-γ$LPGA_n$-C

Conjugation of Br-rPA and Br-rEPA with Type III peptides yielded 4 conjugates:

N-γ$DPGA_n$-$Gly_3$-Cys-S/rPA
N-γ$LPGA_n$-$Gly_3$-Cys-S/rPA
N-γ$DPGA_n$-$Gly_3$-Cys-S/rEPA
N-γ$LPGA_n$-$Gly_3$-Cys-S/rEPA

All eight conjugates precipitated with an identity reaction with their protein and γPGA antisera by immunodiffusion. Representative analysis by MALDI-TOF is shown in FIG. 2.

Conjugation of Br-rEPA with Type VI peptide yielded:

rEPA/Cys-γ$DPGA_n$-N

Conjugation of Br-$rPA_{form}$ with the N-γ$DPGA_n$-$Gly_3$-Cys Type III peptide yielded:

$rPA_{form}$/Cys-$Gly_3$-γ$DPGA_n$-N

Conjugation of Type IV Peptide with BSA, rEPA and rPA Via Hydrazone Linkage 4-formylbenzoyl-DPGA (CHO-γDPGA) was bound to BSA-AH, rEPA-AH or rPA-AH in phosphate buffer, pH 7.0, at a molar ratio of CHO-γDPGA to carrier protein-AH of 2:1 for 24-48 hours at room temperature. The reaction mixture was passed through a 1×90 cm Sepharose CL-6B column in 0.2 M phosphate buffer, pH 7.0, and fractions reacting with anti-carrier protein and anti-γDPGA antibodies were pooled.

Conjugation of BSA-AH, rEPA-AH or rPA-AH with Type IV peptides yielded:

BSA-AH/CHO-$Gly_3$-γ$DPGA_n$-C
rEPA-AH/CHO-$Gly_3$-γ$DPGA_n$-C
rPA-AH/CHO-$Gly_3$-γ$DPGA_n$-C

Conjugation of Type V Peptide With BSA, rEPA, rPA, $rPA_{form}$ Via Hydrazone Linkage Step 1: Derivatization of BSA, rEPA, rPA, or $rPA_{form}$ With SFB To BSA (30 mg) in 1.2 ml of Buffer A containing 1% glycerol, SFB (7.5 mg) in 100 μl DMSO was added and reacted for 1 hour at pH 7.6. The product, 4-formylbenzoyl-BSA (CHO-BSA), was passed through a 1×48 cm Sephadex G-50 column in Buffer A. Protein containing fractions were pooled and assayed for the presence of benzoylaldehyde, antigenicity and protein concentration. For rPA, rEPA and $rPA_{form}$, derivatization with SFB was performed using 4 mg/ml rPA, rEPA and $rPA_{form}$, respectively.

Step 2: Conjugation of CHO-BSA, CHO-rEPA, CHO-rPA or CHO-$rPA_{form}$ with Type V Peptides To CHO-BSA, CHO-rEPA, CHO-rPA or CHO-$rPA_{form}$ (20 mg) in 1.25 ml of Buffer A, 20 mg of Type V peptides dissolved in 400 μl of 1M phosphate buffer, pH 7.4, was added. The pH of the reaction mixture was adjusted to 7.0 and incubated for 48-72 hours at room temperature. The mixture was passed through a 1×90 cm Sepharose CL-6B column in Buffer A, and fractions reacting with anti-carrier protein and anti-γDPGA antibodies were pooled.

Products:

$rPA_{form}$ had 30 out of 58 ϵ-Lys-$NH_2$ free (28 Lys were modified by the formaldehyde treatment), and the derivatization with SFB converted essentially all 30 ϵ-Lys-$NH_2$ into 4-formylbenzoyl-$rPA_{form}$ (CHO-$rPA_{form}$). Conjugation of CHO-BSA, CHO-rEPA, CHO-rPA or CHO-$rPA_{form}$ with Type V peptides yielded:

BSA-CHO/AH-$Gly_3$-γ$DPGA_n$-N
rEPA-CHO/AH-γ$DPGA_n$-N
rPA-CHO/AH-γ$DPGA_n$-N
$rPA_{form}$-CHO/AH-$Gly_3$-γ$DPGA_n$-N Conjugation of BSA-CHO/AH With Type IV Peptide Via Hydrazone Linkage Step 1: Derivatization of BSA With SLV To BSA (56 mg) in 2.0 ml of Buffer A was added SLV (20 mg) in 200 μl DMSO at pH 7.6 and reacted for 1 hour at room temperature. The product, BSA-LV-CHO, was passed through a 1×48 cm Sephadex G-50 column in Buffer A. Protein containing fractions were pooled and assayed for protein concentration.

Step 2: Derivatization of BSA-LV-CHO With ADH

BSA-LV-CHO (35 mg) in 1.5 ml of 0.2 M phosphate buffer, pH 6.0, was reacted with adipic acid dihydrazide (250 mg) at pH 6.0 in the presence of 100 μl of borane-hydride-pyridine complex (800 μmoles) for 48 hours. The product, BSA-LV-CHO/AH, was passed through a 1×48 cm Sephadex G-50 column in Buffer A. BSA containing fractions were collected, analyzed for protein concentration, and the degree of -AH derivatization.

Step 3: Conjugation of BSA-LV-CHO/AH With Type IV Peptide

BSA-LV-CHO/AH (20 mg) in 1.5 ml of 0.2 M phosphate buffer, pH 6.0, was mixed with 10 mg Type IV peptide, pH 6.0. After 60 minutes, 100 μl of borane-hydride-pyridine complex (800 μmoles) was added, and after 48 hours the product was passed through a 1×48 cm Sephadex G-50 column in Buffer A. Fractions reacting with anti-BSA and anti-γDPGA antibodies were pooled.

Conjugation of BSA-LV-CHO/AH with Type IV peptide yielded:

BSA-SL-AH/CHO-Gly$_3$-γDPGA$_n$-C

Immunization

Five- to six-week old female NIH GP mice were immunized s.c. 3 times at 2-week intervals with 2.5 μg γPGA as a conjugate in 0.1 ml of PBS, and groups of 10 mice were exsanguinated 7 days after the second or third injections (Schneerson et al., *J. Exp. Med.* 152:361-76, 1980). Controls received PBS.

Antibodies

Serum IgG antibodies were measured by ELISA (Taylor et al., *Infect. Immun.* 61:3678-87, 1993). Nunc Maxisorb plates were coated with γDPGA, 20 μg/ml PBS or 4 μg rPA/ml PBS. Plates were blocked with 0.5% BSA (or with 0.5% HSA for assay of BSA conjugates) in PBS for 2 hours at room temperature. A MRX Dynatech reader was used. Antibody levels were calculated relative to standard sera: for γDPGA, a hyperimmune murine serum, prepared by multiple i.p. injections of formalin-treated *B. anthracis* strain A34 and assigned a value of 100 ELISA units (EU), for PA a mAb containing 4.7 mg Ab/ml (Little et al., *Infect. Immun.* 56:1807-13, 1988). Results were computed with an ELISA data processing program provided by the Biostatistics and Information Management Branch, CDC (Plikaytis et al., *User's Manual* 12 CDC, Version 1.00, 1996). IgG levels are expressed as geometric mean (GM).

Opsonophagocytosis

Spores of *B. anthracis*, strain A34, were maintained at 5×10$^8$ spores per ml in 1% phenol. The human cell line, HL-60 (CCL240, ATCC, Rockville, Md.) was expanded and differentiated by dimethyl formamide into 44% myelocytes and metamyelocytes, and 53% band and polymorphonuclear leukocytes (PMLs). PMLs were at an effector/target cell ratio of 400:1. PMLs were centrifuged and resuspended in opsonophagocytosis buffer (Hanks' buffer with Ca$^{2+}$, Mg$^{2+}$ and 0.1% gelatin (Life Technologies, Grand Island, N.Y.)) at 2×10$^7$ cells per ml. Spores were cultured at 5×10$^7$ spores per ml for 3 hours in 20% CO$_2$, and diluted to 5×10$^4$ spores per ml. Sera were diluted 2-fold with 0.05 ml of opsonophagocytosis buffer, and 0.02 ml (containing approximately 10$^3$ bacteria) were added to each well of a 24-well tissue culture plate (Falcon, Franklin Lakes, N.J.). The plates were incubated at 37° C. in 5% CO$_2$ for 15 minutes. A 0.01 ml of aliquot of colostrum-deprived baby calf serum (complement) and 0.02 ml of HL-60 suspension containing 4×10$^5$ cells was added to each well, and incubated at 37° C. in 5% CO$_2$ with mixing at 220 rpm for 45 minutes. A 0.01 ml aliquot from each well was added to tryptic soy agar at 50° C., and CFU determined the next morning.

Opsonophagocytosis was defined by ≧50% killing compared with the growth in control wells (Romero-Steiner et al., *Clin. Diagn. Lab. Immunol.* 4:415-33, 1997).

Statistics

ELISA values are expressed as the GM. An unpaired t test was used to compare GMs in different groups of mice.

Example 2

Serum IgG AntiγDPGA Antibodies

This example demonstrates that conjugates of *B. anthracis* γDPGA and of *B. pumilus* γD/LPGA elicited IgG anti-γDPGA antibodies.

Native γDPGA from the capsule of *B. anthracis* elicited trace levels of antibodies after the third injection (Table 1). All the conjugates, in contrast, elicited IgG anti-γDPGA antibodies after two injections (Table 1). Conjugates of *B. anthracis* γDPGA and of *B. pumilus* γD(60%)/L(40%)PGA elicited IgG anti-γDPGA antibodies of intermediate levels after two injections with a booster after the third (Table 1). However, precipitates were formed during the synthesis of both conjugates, resulting in low yields. This problem was not encountered when preparing the synthetic γPGA conjugates.

The highest levels of anti-γDPGA antibodies were achieved with peptide decamers at a density (peptide chains to carrier molecule) of 16:1 for rPA/Cys-Gly$_3$-γDPGA$_{10}$-C, and of 11:1 and 14:1 for rPA-SH/Gly$_3$-γDPGA$_{10}$-C (Table 1). rPA was a more effective carrier than rEPA or BSA (Table 1). With the exception of rPA-SH/Gly$_3$-γDPGA$_{10}$-C, with 11 chains per carrier protein, all conjugates elicited a rise in anti-γDPGA antibodies after the third injection (Table 1). Conjugates prepared with L peptides bound at either the C- or N-terminus induced low levels of IgG anti-γDPGA antibodies (Table 1).

TABLE 1

Composition and serum geometric mean IgG anti-γDPGA and anti-carrier protein antibodies elicited in mice by conjugates of γPGA with BSA, rEPA and rPA.

| Conjugate | Mol γDPGA per mol protein | Protein per γDPGA (wt/wt) | Anti-γDPGA* Second injection | Anti-γDPGA* Third injection | Anti-protein† Second injection | Anti-protein† Third injection |
|---|---|---|---|---|---|---|
| γDPGA-*B. anthracis* | NA‡ | NA | 0.3 | 4.4 | NA | NA |
| rEPA-AH/γDPGA-*B. anthracis* | NA | 1:0.29 | 695 | 2312 | ND§ | ND |
| rPA-AH γDPGA-*B. anthracis* | NA | 1:4.42 | 1325 | 3108 | ND | ND |
| BSA-SH/Gly$_3$-γDPGA$_{10}$-C¶ | 7 | 1:0.14 | 134 | 1984 | ND | ND |
| BSA-SH/Gly$_3$-γDPGA$_{10}$-C | 18 | 1:0.35 | 1882 | 1821 | ND | ND |
| BSA-SH/Gly$_3$-γDPGA$_{10}$-C | 25 | 1:0.49 | 2063 | 2780 | ND | ND |
| BSA-SH/Gly$_3$-γLPGA$_{10}$-C | 7 | 1:0.14 | 261 | 618 | ND | ND |
| rEPA/Cys-Gly$_3$-γDPGA$_{10}$-C | 7 | 1:0.14 | 479 | 4470 | ND | ND |
| rEPA-SH/Gly$_3$-γDPGA$_5$-C | 17 | 1:0.17 | 502 | 1168 | ND | ND |
| rEPA-SH/Gly3-γDPGA$_{10}$-C | 9 | 1:0.18 | 931 | 3193 | ND | ND |
| rEPA-SH/Gly3-γDPGA$_{20}$-C | 5 | 1:0.19 | 749 | 2710 | ND | ND |
| rPA/Cys-Gly$_3$-γDPGA$_5$-C | 32 | 1:0.26 | 2454 | 4560 | 0.06 | 8.5 |
| rPA/Cys-Gly$_3$-γDPGA$_{10}$-C | 16 | 1:0.26 | 9091 | 11268 | 1.30 | 59.3 |

TABLE 1-continued

Composition and serum geometric mean IgG anti-γDPGA and anti-carrier protein antibodies elicited in mice by conjugates of γPGA with BSA, rEPA and rPA.

| Conjugate | Mol γDPGA per mol protein | Protein per γDPGA (wt/wt) | Anti-γDPGA* | | Anti-protein† | |
|---|---|---|---|---|---|---|
| | | | Second injection | Third injection | Second injection | Third injection |
| rPA/Cys-Gly$_3$-γDPGA$_{20}$-C | 14 | 1:0.44 | 742 | 3142 | 0.01 | 4.5 |
| rPA/Cys-Gly$_3$-γDPGA$_5$-N | 22 | 1:0.18 | 3149 | 3460 | 3.70 | 95.0 |
| rPA/Cys-Gly$_3$-γDPGA$_{10}$-N | 21 | 1:0.33 | 5489 | 7516 | 0.10 | 2.2 |
| rPA/Cys-Gly$_3$-γDPGA$_{20}$-N | 8 | 1:0.25 | 2630 | 5461 | 0.05 | 4.9 |
| rPA-SH/Gly$_3$-γDPGA$_5$-C | 15 | 1:0.12 | 1813 | 3607 | 0.27 | 19.7 |
| rPA-SH/Gly$_3$-γDPGA$_{10}$-C | 11 | 1:0.18 | 10460 | 9907 | 0.50 | 102.0 |
| rPA-SH/Gly$_3$-γDPGA$_{10}$-C | 14 | 1:0.22 | 4378 | 7206 | 0.34 | 66.3 |
| rPA-SH/Gly$_3$-γDPGA$_{20}$-C | 4 | 1:0.13 | 2655 | 4069 | 0.90 | 32.2 |
| rPA-SH/Gly$_3$-γDPGA$_{20}$-C | 8 | 1:0.25 | 9672 | 7320 | 0.22 | 189.0 |
| rPA/Cys-Gly$_3$-γLPGA$_{20}$-N | 22 | 1:0.70 | 24 | 79 | 0.14 | 3.0 |
| rPA/Cys-Gly$_3$-γLPGA$_{20}$-C | 24 | 1:0.76 | 155 | 437 | 0.31 | 7.8 |
| BSA-AH/CHO-Gly$_3$-γDPGA$_{10}$-C | 12 | 1:0.23 | 1476 | 3354 | ND | ND |
| rEPA-AH/CHO-Gly$_3$-γDPGA$_{10}$-C | 8 | 1:0.15 | 807 | 2099 | 1 | 14 |
| rPA-AH/CHO-Gly$_3$-γDPGA$_{10}$-C | 22 | 1:0.34 | 1006 | 2478 | 0.3 | 28 |
| BSA-CHO/AH-Gly$_3$-γDPGA$_{10}$-N | 8 | 1:0.17 | 185 | 1139 | ND | ND |
| rEPA-CHO/AH-γDPGA$_{10}$-N | 5 | 1:0.11 | 26 | 483 | 0.1 | 24 |
| rEPA-CHO/AH-γDPGA$_{15}$-N | 6 | 1:0.18 | ND | ND | ND | ND |
| rPA-CHO/AH-γDPGA$_{15}$-N | 5 | 1:0.12 | 119 | 315 | 0.2 | 4 |
| rPA$_{form}$-CHO/AH-Gly$_3$-γDPGA$_{10}$-N | 29 | 1:0.45 | 212 | 1256 | 0.1 | 2 |
| rPA$_{form}$-CHO/AH-γDPGA$_{15}$N | 15 | 1:0.36 | 2158 | 3004 | 0.2 | 6 |
| rPA$_{form}$-CHO/AH-γDPGA$_{15}$N-red | 11 | 1:0.26 | 3619 | 5225 | 0.1 | 13 |
| BSA-SL-AH/CHO-Gly$_3$-γDPGA$_{10}$-C | 3 | 1:0.06 | 103 | 822 | ND | ND |
| TT-CHO/AH-γDPGA$_{15}$-N | 37 | 1:0.48 | 1931 | 2322 | ND | ND |
| rEPA/Cys-γDPGA$_{15}$-N | ND | ND | ND | ND | ND | ND |
| rPA$_{form}$/Cys-Gly$_3$-γDPGA$_{10}$-N | 15 | 1:0.23 | ND | ND | ND | ND |

*γDPGA from *B. anthracis* (strain A34), 2.5 μg as a conjugate used for injection; antibodies by ELISA expressed as EU.
†Antibodies by ELISA expressed as μg Ab/ml.
‡Not applicable
§Not done
¶C or N refers to the free amino acid on the γPGA b

TABLE 4

Formulation effect.

| Conjugate | Dose µg/mouse | Anti-γDPGA 2nd injection | Anti-γDPGA 3rd injection | Anti-rPA 2nd injection | Anti-rPA 3rd injection |
|---|---|---|---|---|---|
| rPA/Cys-Gly$_3$-γDPGA$_{10}$-N | 2.5 | 2231 | 5812 | 2 | 206 |
| | 2.5 + al* | 3527 | 6231 | 80 | 282 |
| rPA/Cys-Gly$_3$-γDPGA$_{10}$-C | 2.5 | 1041 | 2315 | 1 | 185 |
| | 1 | — | 2880 | — | 61 |
| | 1 + form** | — | 2556 | — | 23 |
| | 1 + al | — | 3975 | — | 258 |
| | 1 + form/al | — | 3268 | — | 297 |

*aluminum hydroxide (Alhydrogel)
**formaldehyde treatment (Porro et al., J. Infect. Dis. 142: 716–24, 1980; Nencioni et al., Infect. Immun. 59: 625–30, 1991).

Example 3

Serum IgG Anti-Carrier Protein Antibodies

This example demonstrates that conjugates of *B. anthracis* γDPGA elicited IgG anti-carrier protein antibodies in addition to anti-γDPGA antibodies.

With few exceptions, both the length and number of γDPGA chains per carrier protein were related to the level of IgG anti-carrier protein antibodies (Table 1). Conjugates prepared with γDPGA polypeptides containing 20 residues elicited low levels of carrier protein antibodies (Table 1). Conjugates prepared with either 5 or 10 glutamic acid residues pre chain, and conjugates with <15 chains per carrier protein elicited the highest levels of IgG carrier protein antibodies (Table 1).

Example 4

Opsonophagocytic Activity of Mouse Antisera

This example demonstrates that IgG anti-γDPGA antibodies have opsonophagocytic activity.

Sera from normal mice or those immunized with rEPA or rPA did not have opsonophagocytic activity. However, in mice immunized with BSA-SH/Gly$_3$-γDPGA$_{10}$-C or BSA-SH/Gly$_3$-γDPGA$_{10}$-C there was a correlation between the level of IgG anti-γDPGA antibodies and opsonophagocytosis (r=0.7, P=0.03, Table 5). Addition of γDPGA from *B. anthracis* to the immune sera showed a dose-related reduction of the opsonophagocytic titer of approximately 60%.

TABLE 5

Opsonophagocytic activity and IgG anti-γDPGA antibodies (ELISA) elicited by BSA-SH/Gly$_3$-γDPGA$_{10}$-C.

| Sera | IgG anti-γDPGA | Reciprocal opsonophagocytic titer |
|---|---|---|
| 1196G | 407 | Not detected |
| 1195C | 1,147 | 640 |
| 1197B | 3,975 | 2,560 |
| 1190H | 3,330 | 2,560 |
| 1194D | 3,278 | 2,560 |
| 1193B | 3,178 | 2,560 |
| 1194G | 3,277 | 2,560 |
| 1191J | 5,191 | 5,120 |

Correlation coefficient between ELISA and reciprocal opsonophagocytic titer is 0.7, P = 0.03.

While this disclosure has been described with an emphasis upon certain example, it will be obvious to those of ordinary skill in the art that variations of the examplees may be used and it is intended that the disclosure may be practiced otherwise than as specifically described herein. Accordingly, this disclosure includes all modifications encompassed within the spirit and scope of the disclosure as defined by the claims below.

What is claimed is:

1. An immunogenic conjugate comprising a structure represented by:

X-L-Z wherein X is a carrier selected from BSA, rEPA or rPA;
    Z comprises γPGA; and
    L is a linking group covalently bonded to X and Z, and comprising a structure of —C(O)—(R$^2$)$_y$—C$_6$H$_4$—CH=N—NH—C(O)—(C(R$^6$)$_2$)$_z$—C(O)—NH—NH— wherein R$^2$ is —(CH$_2$)$_n$—C(O)—, or —(CH$_2$)$_n$—N(H)—C(O)—; y is 0 or 1; C$_6$H$_4$ is a benzene ring; n is 1 to 6; z is 1 to 10; and each R$^6$ is hydrogen.

2. The conjugate of claim 1, wherein rPA comprises *B. anthracis* rPA.

3. The conjugate of claim 1, wherein Z comprises *Bacillus* capsular γPGA.

4. The conjugate of claim 2, wherein Z comprises *Bacillus* capsular γPGA.

5. The conjugate of claim 4, wherein the *Bacillus* capsular γPGA is selected from *B. anthracis* γPGA, *B. licheniformis* γPGA, *B. pumilus* γPGA, or *B. subtilis* γPGA.

6. The conjugate of claim 4, wherein Z comprises *B. anthracis* γDPGA.

7. The conjugate of claim 1, wherein n is 4.

8. The conjugate of claim 6, wherein n is 4.

9. The conjugate of claim 1, wherein the carrier comprises rPA.

10. The conjugate of claim 6, wherein the carrier comprises rPA.

11. The conjugate of claim 1, wherein y is 0.

12. The conjugate of claim 1, wherein y is 0 and z is 4.

13. The conjugate of claim 9, wherein z is 4 and y is 0.

14. The conjugate of claim 1, wherein the conjugate elicits an immune response against γPGA in a subject and the conjugate is stable at a pH of about 6 to about 7.5 at room temperature in the presence of glycerol.

* * * * *

UNITED STATES PATENT AND TRADEMARK OFFICE
CERTIFICATE OF CORRECTION

PATENT NO. : 7,625,736 B2  Page 1 of 1
APPLICATION NO. : 11/005851
DATED : December 1, 2009
INVENTOR(S) : Schneerson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 395 days.

Signed and Sealed this

Second Day of November, 2010

David J. Kappos
*Director of the United States Patent and Trademark Office*